US00PP19068P2

(12) United States Plant Patent
Smit

(10) Patent No.: US PP19,068 P2
(45) Date of Patent: Aug. 5, 2008

(54) ***IMPATIENS* PLANT NAMED 'SILTE REEDA'**

(50) Latin Name: *Impatiens walleriana*
Varietal Denomination: Silte Reeda

(75) Inventor: Erik Smit, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/786,130

(22) Filed: Apr. 11, 2007

(51) Int. Cl.
*A01H 5/00* (2006.01)

(52) U.S. Cl. ..... Plt./318.7; Plt./319

(58) Field of Classification Search ..... Plt./318.7, Plt./319
See application file for complete search history.

*Primary Examiner*—Kent L. Bell
*Assistant Examiner*—S. B. McCormick-Ewoldt
(74) *Attorney, Agent, or Firm*—Jondle & Associates, P.C.

(57) ABSTRACT

A new *Impatiens* plant particularly distinguished by double, rose-shaped, red flowers, semi-compact, upright, outwardly spreading and mounded plant habit, free flowering, good basal branching, and moderately vigorous growth habit, is described.

1 Drawing Sheet

Figure 1:
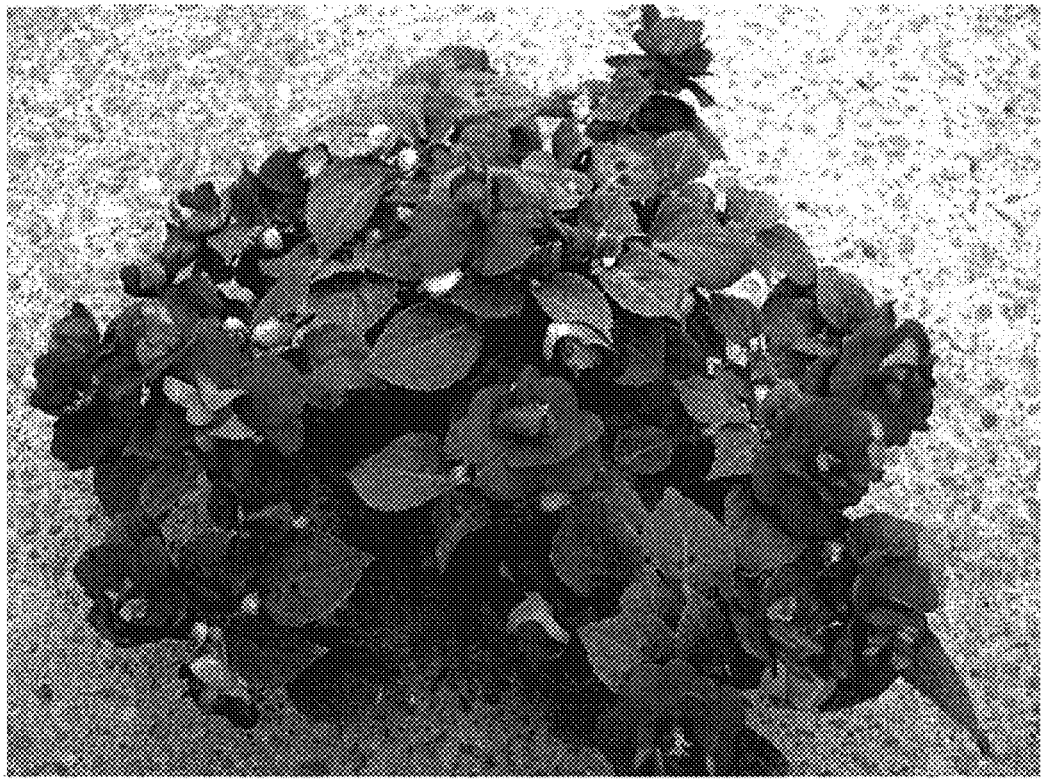

Genus and species: *Impatiens walleriana.*
Variety denomination: 'Silte Reeda'.

BACKGROUND OF THE NEW PLANT

The present invention comprises a new and distinct cultivar of *Impatiens,* botanically known as *Impatiens walleriana,* and hereinafter referred to by the cultivar name 'Silte Reeda'. The new cultivar originated from a controlled self pollination made in January 2003 in Andijk, The Netherlands. The parent was the proprietary red-flowered *Impatiens* plant 'ID03-14-4' (unpatented). The seeds produced by the controlled self pollination were sown in April 2003. A single plant selection was chosen for further evaluation and for asexual propagation in July 2003.

The new cultivar was created in 2003 and has been asexually reproduced repeatedly by vegetative cuttings and tissue culture in Andijk, The Netherlands and Gilroy, Calif. over a three and a half year period. The plant has also been trialed at Gilroy, Calif., Andijk, The Netherlands and Hillscheid, Germany. The present invention has been found to retain its distinctive characteristics through successive asexual propagations.

Plant Breeder's Rights for this cultivar were applied for with the European Union on Nov. 13, 2006.

SUMMARY OF THE INVENTION

The following are the most outstanding and distinguishing characteristics of this new cultivar when grown under normal horticultural practices in Gilroy, Calif. and Andijk, The Netherlands.

1. Double, rose-shaped, red flowers;
2. Semi-compact, upright, outwardly spreading and mounded plant habit; and
3. Free flowering, good basal branching and moderately vigorous growth habit.

DESCRIPTION OF PHOTOGRAPH

This new *Impatiens* plant is illustrated by the accompanying photograph which shows the overall plant habit including blooms, buds, and foliage of the plant; the colors shown are as true as can be reasonably obtained by conventional photographic procedures. The photograph is of a whole plant about 10 weeks old, grown in a greenhouse in Hillscheid, Germany during the spring. The photograph was taken in May 2006 and shows the overall plant habit including blooms, buds, and foliage.

DESCRIPTION OF THE NEW CULTIVAR

The following detailed descriptions set forth the distinctive characteristics of 'Silte Reeda'. The data which defines these characteristics were collected from asexual reproductions carried out in Gilroy, Calif. in a trial setting. The plant history was taken on 26-week-old plants grown in 6-inch containers in a greenhouse during the fall and winter seasons. The plants had one plant growth regulator treatment and one terminal pinch after cuttings were transplanted. Color readings were taken under natural light in the greenhouse in January. Color references are primarily to the R.H.S. Colour Chart of The Royal Horticultural Society of London (R.H.S.) (2001). Texture description data was viewed with a dissecting microscope.

DETAILED BOTANICAL DESCRIPTION OF THE NEW PLANT

Classification:
*Family.*—Balsaminaceae.
*Botanical.*—*Impatiens walleriana.*
*Common name.*—*Impatiens.*

Parentage: 'ID03-14-4' a proprietary red-flowered *Impatiens* plant (unpatented).

Growth:
*Form.*—Semi-compact, upright, outwardly spreading and mounded plant habit.

*Growth and branching habit.*—Free flowering, good basal branching, moderately vigorous, pinching of the terminal apices enhances branching.

*Height* (*from soil level to top of blooms*).—18.0 cm to 20.0 cm.

*Width* (*including flowers*).—50.0 cm to 55.0 cm.

*Time to produce a finished flowering plant.*—About 8 to 10 weeks for a 4-inch pot.

*Outdoor plant performance.*—Use in shade to semi-shade, use in hanging baskets, mixed containers, window boxes and mass plantings.

*Time to initiate and develop roots.*—Approximately 16 to 21 days at 22° C.

*Root description.*—Fibrous, fleshy, white.

Branches:

*Stem.*—Color: RHS 146D with anthocyanin blotches closest to and between RHS 176B and RHS 176D. Length: 24.0 cm to 28.0 cm. Diameter: 0.5 cm to 0.7 cm. Internode length: 1.4 cm to 2.2 cm. Texture: Glabrous.

*Peduncle.*—Color: Between RHS 144B. Length: 3.3 cm to 3.6 cm. Diameter: 0.2 cm. Texture: Glabrous.

Leaves:

*Arrangement.*—Mostly alternate in whorls.

*Size.*—Length: 5.2 cm to 6.0 cm. Width: 3.7 cm to 4.2 cm.

*Shape.*—Ovate.

*Apex.*—Acuminate.

*Base.*—Attenuate.

*Margin.*—Crenate with ciliation.

*Color* (*immature leaves*).—Upper surface: Lighter than RHS 139A. Lower surface: RHS 147B with RHS 176B blotches of anthocyanin.

*Color* (*mature leaves*).—Upper surface: Closest to RHS 139A. Lower surface: RHS 147B with RHS 176B blotches of anthocyanin.

*Texture.*—Glabrous.

*Venation color.*—RHS 145A.

*Petioles.*—Length: 1.3 cm to 1.5 cm. Diameter: 0.2 cm. Color: RHS 145C. Texture: Glabrous.

Flower buds:

*Shape.*—Ovate.

*Size.*—Length: 1.2 cm to 1.5 cm. Diameter: 1.1 cm to 1.4 cm.

*Color at tight bud.*—RHS 39A.

Inflorescence:

*Blooming habit.*—Continuous and freely, all through the year, depending on light levels.

*Type.*—Raceme in leaf axis.

*Number of flowers per inflorescence.*—6 to 8.

*Lastingness of the individual blooms.*—About 5 to 7 days depending on environmental conditions.

*Fragrance.*—None.

Flowers:

*Form and shape of corolla.*—Double-type, rose-shaped bud opening to form a full round flower.

*Corolla size.*—Width: 4.5 cm to 5.0 cm. Depth: 2.3 cm to 2.5 cm.

*Number of petals per flower.*—25 to 35.

Petals:

*Shape.*—Broadly obovate.

*Apex.*—Round to obtuse.

*Base.*—Attenuate.

*Margin.*—Entire.

*Petal size.*—Length: 2.0 cm to 2.2. Width: 1.4 cm to 2.0 cm.

*Color.*—Immature petals: Upper surface: RHS 45A. Lower surface: RHS 50B. Mature petals: Upper surface: RHS 45A but a little more blue in the red. Lower surface: RHS 50B.

*Texture.*—Papillose; velvety and luminescent.

Sepals:

*Quantity.*—5; 2 large sepals, 1 modified sepal with a spur and 2 small sepals.

*Texture.*—Glabrous.

*Large sepals.*—Color: RHS 155C; RHS 143B keel. Length: 0.9 cm to 1.0 cm. Width: 1.0 cm to 1.1 cm. Shape: Broadly ovate. Apex: Cuspidate. Base: Fused. Margin: Entire. Spur: Color: RHS 174C; RHS 173A at the apex. Length: 3.0 cm to 3.3 cm. Diameter: 0.1 cm.

*Small sepals.*—Color: RHS 143B. Length: 0.2 cm. Width: 0.1 cm. Shape: Ovate. Apex: Acute. Margin: Entire. Base: Fused.

Reproductive organs: Usually not developed and observed.

Fruit and seed set: No seed set observed.

Disease and insect resistance: No particular resistance or susceptibility has been observed.

COMPARISON WITH PARENTAL AND COMMERCIAL CULTIVARS

'Silte Reeda' differs from the parent 'ID03-14-4' in that 'Silte Reeda' has a double flower, while 'ID03-14-4' has a single flower. Additionally, 'Silte Reeda' has lighter foliage and a more compact plant habit than 'ID03-14-4'.

'Silte Reeda' differs from the commercial cultivar 'Balfiesaled' (U.S. Plant Pat. No. 16,626) in that 'Silte Reeda' has more yellow-green color on the underside of the foliage than 'Balfiesaled'. 'Silte Reeda' has more brownish anthocyanins, while 'Balfiesaled' has more red anthocyanins. Additionally, 'Silte Reeda' has a shorter petiole and brownish sepals, with a little lighter blue-red flower than 'Balfiesaled'.

I claim:

1. A new and distinct cultivar of *Impatiens* plant as shown and described herein.

* * * * *